United States Patent [19]

Abe et al.

[11] 4,202,775
[45] May 13, 1980

[54] ADSORBENT FOR ADSORBING ORGANIC COMPOUNDS ADSORBED ON PROTEINS

[75] Inventors: Tsutomu Abe, Fuji; Akihiko Ikeda, Yokohama; Tokio Sakurai, Nobeoka, all of Japan

[73] Assignee: Asahi Kasei Kogyo Kabushiki Kaisha, Osaka, Japan

[21] Appl. No.: 917,828

[22] Filed: Jun. 22, 1978

[30] Foreign Application Priority Data

Jun. 24, 1977 [JP] Japan .................................. 52-74516
Jul. 5, 1977 [JP] Japan .................................. 52-80338

[51] Int. Cl.² ............................................. B01D 15/04
[52] U.S. Cl. .............................. 210/287; 210/DIG. 23; 521/29; 521/38; 424/79
[58] Field of Search ......... 210/287, 24, 263, DIG. 23, 210/40, 502; 128/214 B; 424/10, 78, 101; 23/258.5 R; 521/38, 29

[56] References Cited

U.S. PATENT DOCUMENTS

| | | | |
|---|---|---|---|
| 3,531,463 | 9/1970 | Gustafson | 210/24 R |
| 3,663,467 | 5/1972 | Albright | 210/24 R |
| 3,794,584 | 2/1974 | Kunin | 210/24 R |
| 4,064,042 | 12/1977 | Kunin | 210/DIG. 23 |

Primary Examiner—Benoit Castel
Attorney, Agent, or Firm—Sprung, Felfe, Horn, Lynch & Kramer

[57] ABSTRACT

An adsorbent comprising a porous copolymer produced by copolymerizing a cross-linkable monomer and a mono-ethylenically unsaturated monomer, said copolymer having pores of an average pore diameter (d) of 500 Å to 6,000 Å and having such a broad pore diameter distribution that the pore volume having a pore diameter in the range of from 0.5 d to 2 d is not more than 60% of the total pore volume in the copolymer. By the use of such a porous copolymer having a specific composition and pore characteristics, organic compounds (e.g. toxic compounds) adsorbed on the proteins (e.g. plasma proteins) present in intercellular and/or extracellular liquids (e.g. blood) can be effectively adsorption-removed. Especially when the present adsorbent is used for purification of blood, it is advantageously subjected to such a pretreatment that plasma proteins are adsorbed on the adsorbent and then crosslinked with a crosslinking agent. The pretreated adsorbent can prevent unfavorable adsorption of blood platelets and leukocytes thereon. The present adsorbent is quite suitable for use in a column type purifier apparatus.

8 Claims, 3 Drawing Figures

ADSORBENT FOR ADSORBING ORGANIC COMPOUNDS ADSORBED ON PROTEINS

The present invention relates to an adsorbent for adsorbing organic compounds from proteins present in an extracellular and/or intracellular liquid, and more particularly to an adsorbent for adsorbing organic compounds adsorbed on the proteins.

When organic compounds are present together with proteins in an aqueous solution such as an intracellular and/or extracellular liquid, the organic compounds and the proteins are present often in such a state that they are mutually adsorbed. The adsorptions between the organic compounds and the proteins are considered to be due to various bonds such as hydrophobic bond, ionic bond, hydrogen bond, bond by van der Waals' force, and combinations thereof.

The term "hydrophobic bond" as used herein means a phenomenon that checmical compounds having hydrophobic regions in their chemical structures tend to associate together in an aqueous solution.

The term "intracellular liquid" as used herein means an aqueous solution of proteins filled in a cell enclosed by a biomembrane, and the term "extracellular liquid" means, in the case of higher animals, an aqueous solution of proteins present outside the cells, for example, lymph, cerebrospinal fluid, ascites, etc., and in the case of lower animals, liquid environments containing proteins necessary to maintain their life, for example, a culture mother liquid etc.

Blood is regarded as a special case where single cells are suspended in an extracellular liquid called blood plasma, and in light of the object of the present invention blood is considered one of extracellular liquids. In more special case where blood cells are collapsed, the blood is considered a mixture of an intracellular liquid and an extracellular liquid.

The organic compounds to be adsorbed onto the adsorbent of this invention include all kinds of natural or synthetic organic compounds having a property to be adosrbed on proteins present in the intracellular or extracellular liquids.

Specific examples of the organic compounds include substances produced by metabolism such as unconjugated bilirubin, basoflavins, ascorbic acid, acetylcholine, adenosine, free carboxilic acids, bile acids, triiodothyronine, thyroxine, cortisol, histamines, and vitamins A, K, D and E; physiologically active substances such as Chloromycetin, digitonin, Neosalvarsan, Aureomycin, penicillins, salicylic acid and barbituric acid and its derivertives, e.g. phenobarbital; dyes such as Indocyanine Green, sulfobromophthalein, Bromocresol Green, Phenol Red and Congo Red; non-active antagonistic and nonantagonistic inhibitors against enzymes which are not bonded to a biomembrane; various immunogens and haptenes; solubilizers for proteins such as anionic surface active agents, e.g. alkylbenzenesulfonic acid sodium salts and sodium lauryl sulfate, cationic surface active agents, e.g. cetyl pyridinium chloride, and non-ionic surface active agents, e.g. polyoxyethylene sorbitan monooleates, para-isooctylphenyl polyoxyethylene ether polymers; and other various organic compounds adsorbed on the proteins present in the industrial wastes such as in the spent culture media or the collapsed fungi-containing liquids which are obtained in the industries of fermentation such as amino acid fermentation, nucleic acid fermentation, organic acid fermentation, and fermentations for antibiotics, physiologically active substances, enzymes and proteins released from bacteria, fungi and the like.

In the prior techniques, it is generally very difficult to detach organic compounds from the proteins on which the organic compounds are adsorbed, by adsorbing the organic compounds onto adsorbents without impairing the properties of the proteins.

By the use of an adsorbent according to the present invention, it has for the first time become possible to realize easy detachment and adsorption of the organic compounds as mentioned above.

Essentially, according to the present invention, there is provided an adsorbent for adsorbing organic compounds from proteins on which said organic compounds are adsorbed in an intracellular and/or extracellular liquid, which comprises a porous copolymer produced by copolymerizing a mixture of monomers consisting essentially of 2 to 99% by weight of at least one crosslinkable monomer and 1 to 98% by weight of at least one mono-ethylenically unsaturated monomer, said porous copolymer having pores of an average pore diameter (d) in the range of from 500 Å to 6,000 Å, the volume of pores of a pore diameter in the range of from 0.5 d to 2 d being not more than 60% of the total pore volume in said porous copolymer.

The adsorbent according to the present invention is in the form of granules having a diameter in the range of 20 to 1,000μ, preferably 50 to 500μ.

In another aspect of the present invention, there is provided an adsorbent of the character described, which has blood plasma proteins adsorbed thereon and fixed thereto, said blood plasma proteins being insolubilized by crosslinkage between the proteins and a crosslinking agent.

In a further aspect of the present invention, there is provided a purifier apparatus containing therein the adsorbent as defined above.

The copolymer of the present invention has a three-dimensional network and therefore the molecular weight of the present copolymer cannot be specifically defined as that of linear polymers. Due to the three-dimensional network, the copolymer is not dissolved in a solvent and hence the chemical structure of the copolymer cannot be identified as in the case of linear polymers whose chemical structure can be identified from physical properties of their solutions such as viscosity or diffusion of light. The copolymer of this invention cannot also be spectroscopically analysed even by ultra-violet absorption spectrophotometry, nuclear mangetic resonance spectrometry or the like.

As the polymerizable mono-ethylenically unsaturated monomer which constitutes one recurring unit of the adsorbent of the present invention, a wide variety of monomers may be used. Specific examples of such monomers include hydrocarbon monomers such as styrene, methylstyrenes, ethylstyrenes, propylstyrenes, butylstyrenes, pentylstyrenes, diphenylethylenes, vinylnaphthalenes, vinylphenanthrenes, vinylmesitylene, 3,4,6-trimethylstyrene, 1-vinyl-2-ethylacetylene; styrene derivatives such as chlorostyrenes, methoxystyrenes, bromostyrenes, cyanostyrenes, fluorostyrenes, dichlorostyrenes, N,N-dimethylaminostyrenes, nitrostyrenes, chloromethylstyrenes, trifluorostyrenes, trifluoromethylstyrenes and aminostyrenes; vinyl sulfide derivatives such as methyl vinyl sulfide and phenyl vinyl sulfide; acrylonitrile; methacrylonitrile; acrylonitrile derivatives such as α-acetoxyacrylonitrile; acrylic acid, methacrylic acid; acrylates such as methyl acrylate, lauryl acrylate and chloromethyl acrylate; acetoxyacrylates such as ethyl acetoxyacrylate; methacrylates such as cyclohexyl methacrylate, dimethylaminoethyl methacrylate, glycidyl methacrylate, tetrahydrofurfuryl methacrylate and hydroxyethyl methacrylate; diethyl maleate; diethyl fumarate; vinyl ketones such as methyl vinyl ketone and ethyl isopropenyl ketone; vinylidene compounds such as vinylidene chloride, vinylidene bromide, and vinylidene cyanide; acrylamide and its derivatives such as methacrylamide, N-butoxymethyl acrylamide, N-phenyl acrylamide, diacetone acrylamide, N,N-dimethylaminoethyl acrylamide; vinyl esters of fatty acids such as vinyl acetate, vinyl lactate and vinyl caprate; thiofatty acid derivatives such as phenyl thiomethacrylate and methyl thioacrylate; and heterocyclic vinyl compounds such as N-vinylsuccinimide, N-vinylpyrrolidone, N-vinylphthalimide, N-vinylcarbazole, vinylfurans, 2-vinylbenzofuran, vinylthiophenes, vinylimidazoles, methylvinylimidazoles, vinylpyrazoles, vinyloxazolidones, vinylthiazoles, vinyltetrazoles, vinylpyridines, methylvinylpyridines, 2,4-dimethyl-6-vinyltriazine and vinylquinolines. They may be employed either alone or in mixture. Of them, preferred are styrene, and styrenes substituted with 1 to 3 straight chain or branched ($C_1$-$C_5$) alkyl groups such as methyl, ethyl, n-propyl, iso-propyl, n-butyl, sec-butyl, tert-butyl and the like or mixtures thereof, with a view point of sanitariness as well as thermal stability required in the heat-sterilization, if any.

The term "cross-linkable monomer" as used herein is intended to mean a monomer having a plurality of $CH_2=C<$ groups.

As specific examples of the cross-linkable monomer which constitutes the other recurring unit of the copolymer of the adsorbent of the present invention, there can be mentioned divinylbenzenes, divinyltoluenes, divinylxylenes, divinylnaphthalenes, divinylethylbenzenes, divinylphenanthrenes, trivinylbenzenes, divinyldiphenyls, divinyldiphenylmethanes, divinyldibenzyls, divinylphenyl ethers, divinyldiphenylsulfides, divinyldiphenylamines, divinyl sulfone, divinyl ketone, divinylfurans, divinylpyridines, divinylquinolines, di(vinylpyridinoethyl)ethylenediamine, diallyl phthalate, diallyl maleate, diallyl fumarate, diallyl succinate, diallyl carbonate, diallyl oxalate, diallyl adipate, diallyl sebacate, diallyl tartrate, diallylamine, triallylamine, triallyl phosphate, triallyl tricarballylate, triallyl aconitate, triallyl citrate, N,N'-ethylenediacrylamide, N,N'-methylenediacrylamide, N,N'-methylenedimethacrylamide, ethylene glycol diacrylate, polyethylene glycol diacrylates, ethylene glycol dimethacrylate, polyethylene glycol dimethacrylates, propylene glycol diacrylate, polypropylene glycol diacrylates, propylene glycol dimethacrylate, polypropylene glycol dimethacrylates, trimethylolpropane trimethacrylate, pentaerythritol tetramethacrylate, 1,3-butylene glycol diacrylate, 1,6-hexanediol diacrylate, trimethyl propane triacrylate, pentaerythritol tetraacrylate, triallyl isocyanurate, 1,3,5-triacryloylhexahydro-1,3,5-triazine, and diallyl melamine. They may be employed either alone or in mixture. Preferred cross-linkable monomers are divinylbenzene, ethylene glycol diacrylate, polyethylene glycol diacrylates, ethylene glycol dimethacrylate, polyethylene glycol dimethacrylates, propylene glycol diacrylate, polypropylene glycol diacrylates, propylene glycol dimethacrylate and polypropylene glycol dimethacrylates. In this invention, the terms "polyethylene glycol diacrylates", "polyethylene glycol dimethacrylates", "polypropylene glycol diacrylates" and "polypropylene glycol dimethacrylates" as mentioned above include also the oligomers such as the dimers, trimers and the like and are generally defined as the polymers having a weight average molecular weight of up to 1,500, the weight average molecular weight being measured in accordance with ASTM D 3536.

The content of the cross-linkable monomer in the copolymer of this invention is in the range of from 2 to 99% by weight and preferably from 5 to 90% by weight. When the content of the cross-linkable monomer is too low, swelling or contraction of the copolymer is unfavorably increased and its mechanical strength is decreased.

The porous copolymer, i.e. the adsorbent, according to the present invention may be produced by the process as disclosed in J. Seidel & J. Malinsky, Adv. Polymer Sci., 5, 113 (1967). More specifically, the present adsorbent can advantageously be produced by the process as disclosed in Deutsche Offenlegungsschrift No. 2,618,481.

One of methods for preparing adsorbent copolymers of the present invention will now be described.

The content of the mono-ethylenically unsaturated monomer in the polymer of this invention may be in the range of from 1 to 98% by weight and preferably from 10 to 95% by weight.

The adsorbent of the present invention can be produced by copolymerizing a monomer mixture comprising 2 to 99% by weight of at least one cross-linkable monomer and 1 to 98% by weight of at least one mono-ethylenically unsaturated monomer in the presence of an organic medium which does not react with any of the monomers, selected from the group consisting of (1) a mixed organic medium consisting of at least one liquid selected from Group (i) and at least one liquid selected from Group (iii);
(2) a mixed organic medium consisting of at least one liquid selected from Group (ii) and at least one liquid selected from Group (iii);
(3) a mixed organic medium consisting of at least two liquids selected from Group (iii);
(4) an organic medium consisting of one liquid selected from Group (iii);
(5) a mixed organic medium consisting essentially of at least one liquid selected from Group (i) and at least one liquid selected from Group (ii);
(6) an organic medium consisting of one liquid selected from Group (ii); and
(7) a mixed organic medium consisting of at least two liquids selected from Group (ii)

wherein
  Group (i): organic liquids which dissolve all of the homopolymers of the monomers chosen;
  Group (ii): organic liquids which do not dissolve any of the homopolymers of the monomers chosen; and
  Group (iii): organic liquids which dissolve at least one homopolymer of the monomers chosen but do not dissolve at least another homopolymer of the monomers chosen.

In the present invention, the following method is employed for selecting an organic liquid.

To one organic liquid is added 5 percent by weight of one monomer and 0.1 percent by weight of 2,2-azobisisobutyronitrile and the resulting solution is polymerized in a sealed glass tube for 8 hours at the same temperature as is to be used for the polymerization reaction of this invention, and then the reaction mixture is observed. When the resulting polymer is precipitated, the organic liquid is denoted an "organic liquid which does not dissolve a homopolymer of the monomer", and when the resulting polymer is dissolved in the organic liquid, the organic liquid is denoted an "organic liquid which dissolves a homopolymer of the monomer". Also, with regard to one cross-linkable monomer having a plurality of $CH_2=C<$ groups employed as the monomer, when the reaction mixture of the resulting polymer and the organic liquid is opaque, the organic liquid is denoted an "organic liquid which does not dissolve a homopolymer of the monomer", and when the reaction mixture is transparent, the organic liquid is denoted an "organic liquid which dissolves a homopolymer of the monomer".

The solubilities of certain polymers in organic liquids are described in J. Brandrup and E. H. Immergut, *Polymer Handbook*, Chap. IV, pages 185–234 (1966) and Chap. IV, pages 241–265, Second Edition (1975) which is useful when selecting solvents and non-solvents.

The process for the preparation of a copolymer having a desired porous structure will now be explained.

Firstly, the desired pore diameter can be obtained in accordance with the following procedures. The polymerization is carried out using an organic medium containing at least one appropriate liquid selected from Group (iii) liquids. When the pore diameter of a polymer obtained is smaller than that desired, it can be increased by adding at least one liquid selected from Group (ii) liquids to the organic medium. When the pore diameter is greater than that desired, it can be decreased by adding at least one liquid selected from Group (i) liquids to the organic medium. When an organic medium containing at least two liquids selected from Group (iii) liquids is employed, the pore diameter can be controlled precisely. Generally, when there are employed a plurality of liquids, the pore diameter in the resulting copolymer can be continuously changed by appropriately changing the mixture ratio of the liquids.

Secondly, the desired pore volume can be obtained by controlling following conditions. The pore volume of the resulting copolymer depends on its pore diameter and on the amount of the organic medium employed. When the pore diameter is small, most of the organic medium is consumed for swelling of the polymer network and, as a result, the pore volume is decreased. On the other hand, as the proportion of the crosslinkable monomer to the total monomers is increased, it is required for securing sufficient pore volume to increase the amount of the organic medium to be added. One of the reasons for this is that while the swelling tendency of a low cross-linked copolymer in an aqueous solution leads to increase of its pore volume, a high cross-linked copolymer has less such tendency and therefore the increase of its pore volume due to swelling in an aqueous solution is smaller. Another reason is that the higher the degree of cross-linking, the denser the three-dimensional structure of the polymer chain of the resulting copolymer becomes and therefore, the harder it becomes to form micropores which provide adsorption sites for organic compounds to be adsorbed thereon. More specifically, if the percent by weight of the total liquids based on the total monomers is designated as D and the percent by weight of the cross-linkable monomer based on the total monomers is designated as X, it is advantageous that the conditions of $7\sqrt{X}<D<500\sqrt{X}$ are satisfied, and it is more advantageous that the conditions of $20\sqrt{X}<D<200\sqrt{X}$ are satisfied and most advantageous that the conditions of $34\sqrt{X}<D<150\sqrt{X}$ are satisfied.

Specific examples of combinations of liquids to be used for the preparation of copolymers of the present invention will now be mentioned.

(I) When a monomer mixture consists essentially of (a) at least one monomer selected from divinylbenzenes, ethylene glycol dimethacrylate, polyethylene glycol dimethacrylates, propylene glycol dimethacrylate, polypropylene glycol dimethacrylates, ethylene glycol diacrylate, polyethylene glycol diacrylates, propylene glycol diacrylate and polypropylene glycol diacrylates and (b) at least one monomer selcted from styrene, ethylvinylbenzenes and methyl methacrylate, Group (i) includes benzene, toluene, xylenes, ethylbenzene, tetraline, ethyl acetate, dioxane, ethylene chloride, nitromethane, nitroethane, chlorobenzene, dichlorobenzenes, cyclohexanone, pyridine, benzyl alcohol, and anisole; and Group (ii) includes propanols, butanols, hexanols, octanols, hexanes, heptanes, cyclohexanes, dioctyl phthalate and didodecyl phthalate, (II) When a monomer mixture consists essentially of (a) at least one monomer selected from ethylene glycol dimethacrylate and divinylbenzenes, (b) at least one monomer selected from 2-vinylpyridine and 2-methyl-5-vinylpyridine, and (c) at least one monomer selected from styrene, ethylvinylbenzenes, methyl methacrylate, and methyl acrylate, Group (i) includes benzene, toluene, xylenes, cyclohexanone, methyl ethyl ketone, anisole, methyl benzoate, ethyl benzoate, ethyl propionate, dimethyl phthalate, benzonitrile, nitropropane, chlorobenzene and o-dichlorobenzene; Group (ii) includes hexanes, cyclohexane, heptanes and octanes; and Group (iii) includes butanols, pentanols, hexanols, cyclohexanol and octanols.

(III) When a monomer mixture consists essentially of: (a) at least one monomer selected from ethylene glycol dimethacrylate and divinylbenzenes, (b) at least one monomer selected from styrene, ethylvinylbenzenes, methyl methacrylate, 2-vinylpyridine and 2-methyl-5-vinylpyridine, and (c) at least one monomer selected from acrylonitrile and methacrylonitrile, Group (ii) includes hexanes, cyclohexane, heptanes, octanes, decanes, pentanols, hexanols, cyclohexanols and octanols; and Group (iii) includes benzene, toluene, xylenes, chlorobenzene, ethylbenzene, ethyl acetate, methyl propionate, butyl propionates, butyl adipates, methyl benzoate, ethyl benzoate and diethyl phthalate. Furthermore, when only acrylonitrile is selected from the above described group (c), Group (iii) additionally includes propionitrile, n-butyronitrile, nitroethane, nitropropane, methyl ethyl ketone, methyl isobutyl ketone and cyclohexanone.

(IV) When a monomer mixture consists essentially of: (a) at least one monomer selected from ethylene glycol dimethacrylate, polyethylene glycol dimethacrylates and divinylbenzenes, (b) at least one monomer selected from styrene, ethylvinylbenzenes, methyl methacrylate and 2-vinylpyridine, and (c) N-vinylpyrrolidone, Group (ii) includes hexanes, cyclohexane, heptanes and decanes; and Group (iii) includes ethyl acetate, butyl propionates, benzyl acetate, diisopropyl ketone, benzene, toluene, ethylbenzene and tetraline.

The peculiar adsorption characteristcs of the copolymer of this invention depends mainly upon a porous structure of the copolymer. A porous structure is specified by an average pore diameter, pore diameter distribution, a total pore volume etc. It is required for the present porous copolymer that the pores in the copolymer have an average pore diameter of from 500 Å to 6,000 Å, preferably 600 Å to 5,000 Å. If the average pore diameter is too small, the amount and rate of adsorption of organic compounds on the copolymer is reduced, and if the average diameter is too large, the strength of the copolymer is lowered and hence the copolymer is not adapted to practical use, and furthermore the surface of the copolymer is inevitably very small, resulting in a poor adsorbing capacity of the adsorbent. Also the pore diameter distribution is a factor having a significant influence on the adsorbing capacity. It is necessary that the proportion of pores having a diameter of 0.5 d to 2 d (in which d designates the average pore diameter) be not more than 60%, and it is more preferred that the proportion of such pores be not more than 50% of the total pore volume. Although there is specified no lower limit of this value, it is generally preferred that the proportion of pores having an above-specified diameter be at least 30%.

In the copolymer of the present invention, it is advantageous that the total pore volume is in the range of from $0.15\sqrt{X}$ ml to $1.3\sqrt{X}$ ml per gram of the dry copolymer, in which X stands for the weight percent of the cross-linkable monomer expressed in terms of the percent by weight based on the total monomers. It is more advantageous that the total pore volume is in the range of $0.5\sqrt{X}$ ml to $1.0\sqrt{X}$ ml per gram of the dry copolymer, and it is most advantageous that the total pore volume is in the range of from $0.2\sqrt{X}$ ml to $0.8\sqrt{X}$ ml per gram of the dry copolymer. When the pore volume is too small, no sufficient adsorbing surface is provided. If the pore volume is too large, not only is the mechanical strength of the copolymer decreased, but also the adsorbing capacity, that is the amount of organic compounds that can be adsorbed per unit volume of the copolymer, is rather reduced.

Methods adopted in the present invention for the determination of pore characteristics will now be described.

The average pore diameter, pore diameter distribution and pore volume are measured using a mercury penetration porosimeter. More specifically, mercury is forced, under increasing pressure, into the pores of the porous material to be measured and the pore volume is determined from the amount of mercury occluded in pores of the sample, and the pore diameter is calculated based on the principle that the diameter of a pore is in inverse proportion to the pressure necessary for forcing mercury into the pores. This measurement method is detailed in Chapter 10 of "Fine Particle Measurement" written by Clyde Orr, Jr. and J. M. Dallavalle and published by The Macmillan Company, New York in 1959, and also in "Industrial and Engineering Chemistry" vol. 17, No. 12, 1945, p. 782 to 786, written by H. L. Ritter and L. C. Drake. The measurement may be conducted basically in accordance with ANSI/ASTM D2873-70 (Reapproved 1976), using a Mercury Penetration Porosimeter, Model 905-1 (manufactured and sold by Micromeritics Instrument Corporation, U.S.A.). Penetration volume readings may be obtained by forcing mercury into the pores at the pressures (psi) in the following list:

| | | | | |
|---|---|---|---|---|
| 14.7 | 100 | 450 | 2,000 | 10,000 |
| 20 | 125 | 650 | 3,000 | 15,000 |
| 35 | 175 | 850 | 4,000 | 20,000 |
| 45 | 250 | 1,150 | 5,000 | 30,000 |
| 85 | 350 | 1,500 | 7,000 | 40,000 |
| | | | | 50,000 |

According to this method, even pores having a pore diameter as small as 35–40 Å can be measured. In the present invention, the term "pore" is intended to mean an open pore communicated with the outside surface of the copolymer and having a pore diameter of at least 40 Å, and the pore volume is determined with respect to such open pores. The porosimeter readings versus the total absolute pressure may be plotted on four phase semilog graph paper and the points connected using a French curve. The obtained curve represents a profile of the apparent interval pore size distribution. The "average pore diameter" is defined to be a value of r providing a maximum value of dV/d log r in the obtained curve, in which r represents the pore diameter and V denotes the cummulative pore volume measured by the mercury penetration porosimeter. In the present invention, the "total pore volume" is defined to be the volume of mercury forced in the pores of 1 g. of the sample dry copolymer during the period in which the mercury pressure is increased from 56 psi to 50,000 psi in the mercury penetration method.

The bulk density of the copolymer in the dry state can be mentioned as another index of porosity. In the present invention, the bulk density was determined according to the following method: A sample copolymer was charged in a column equipped with a glass filter, water was passed through the column and the volume of the sample-packed portion of the column was measured. Then, the sample was sufficiently dried and its weight was measured. The bulk density was calculated by dividing the weight by the volume. The bulk density as defined above of the present copolymer in the dry state is in the range of 0.05 to 0.5 g/ml preferably 0.1 to 0.4 g/ml and more preferably 0.15 to 0.3 g/ml.

The term "dry copolymer" or "copolymer in the dry state" as used herein is intended to mean a copolymer, the weight of which has become substantially constant upon the following drying process. After copolymerization, the obtained copolymer is thoroughly washed with a solvent having a boiling point not higher than 120° C., and is then dried at 70° C. The weight of the copolymer is measured at prescribed intervals. When the difference between two measured weights of the copolymer at an interval of 24 hours is less than 1% of the later measured weight, the copolymer is regarded as the copolymer of which the weight has become substantially constant. Drying may be conducted under reduced pressure so as to shorten the drying time.

The copolymer produced by the aforementioned method has a broad pore diameter distribution range as described hereinbefore. Large-diameter pores serve to remarkably increase the velocity of diffusion and permeation of proteins, on which organic compounds are adsorbed, into the pores of the copolymer and accelerate a rate of adsorption of organic compounds onto the copolymer, while the presence of small-diameter pores increases the surface area of the pores and consequently increases the adsorption capacity of the copolymer. The co-presence of large-diameter pores and small-diameter pores is a characteristic feature of the copolymer of this invention. It is believed that in the copolymer of the present invention the large-diameter pores are present uniformly in the surface portions and the interior of the copolymer and the small-diameter pores are present in the copolymer at its surface portions and/or at the inner wall portions of the large-diameter pores.

The copolymer of this invention can be easily produced in a spherical form by a suspension polymerization method and it has a high mechanical strength. Accordingly, the present porous copolymer is quite suitable for use in a column type purifier apparatus as will be mentioned later. The copolymer of this invention is advantageous in that it is insoluble in water and organic solvents. Further, it is noted that according to the application field, by appropriately choosing a kind and an amount of the monomer, it is easily possible to prepare a porous copolymer having not only a sufficient inactivity to substances present in the environments of the application field but also a stability to the pH conditions of the environments.

The mechanism of separation of organic compounds from proteins by adsorption onto the copolymer of the present invention is not exactly known in detail, but is believed as follows. The proteins with organic compounds adsorbed thereon diffuse and permeate into the pores of the copolymer and are adsorbed on the surface of the internal pores of the copolymer. In such a state, the organic compounds cannot be detached from the proteins. It is expected that when the adsorption force between the organic compounds and the copolymer is greater than that between the organic compounds and the protein, only the organic compounds may be adsorbed on the copolymer. The copolymer adsorbent of this invention provides a high adsorption force between the organic compounds and the adsorbent. By contacting the adsorbent with a liquid such as an intracellular liquid, extracellular liquid or blood, organic compounds present in the liquid and adsorbed on proteins can be readily separated from the proteins.

By an adsorption method wherein an aqueous protein solution to be treated is flowed through a column packed with the adsorbent of this invention or an adsorption method wherein the adsorbent of this invention is added to an aqueous protein solution to be treated, organic compounds such as antibiotics, physiologically active substances and terminal metabolites which are adsorbed on the proteins can be easily separated and taken out of the proteins, and also surface active agents which are adsorbed on proteins can be easily removed.

Blood is such a liquid that blood cells are suspended in plasma. In plasma, most of organic compounds are adsorbed on plasma proteins such as albumin and β-lipoprotein. When the organic compounds in the blood are removed, using the present adsorbent, from the blood, it is necessary to prevent blood platelets and leukocytes from being adsorbed onto the surface of the adsorbent. For this purpose, the plasma may usually be separated by means of a centrifugal separator and is then treated with the adsorbent. In the case of a continuous operation, it is preferred to treat the blood by a method wherein the plasma is continuously separated by filtration with a porous membrane or a method wherein the plasma is continuously separated by means of a continuous centrifugal separator, and then, to continuously contact only the separated plasma with the adsorbent packed in a column. In particular, in order to restrain the loss of the blood platelets at a minimum level, it is more preferred to use, among various plasma separators using a porous membrane, a plasma separator comprising cellulose acetate hollow fibers as a porous membrane (see, e.g. Japanese Patent Application Laid-Open Specification No. 93786/1976).

As another method for prevention of adsorption of blood platelets and leukocytes, the copolymer adsorbent may be pretreated with a plasma protein as follows. The plasma protein such as human albumin is adsorbed on the copolymer adsorbent, and thereafter the protein is partially modified by a cross-linking agent so that it is insolubilized and fixed onto the copolymer adsorbent. By this pretreatment, the adsorption of blood platelets and leukocytes on the adsorbent can be effectively prevented. In the adsorbent of this invention, even after this pretreatment there is not recognized significant lowering of the adsorbing capacity of the adsorbent.

Any kind of crosslinking agents may be used for such pretreatment so far as it has in its molecule two or more reactive groups capable of forming covalent bonds together with amino and/or carboxyl group in the protein molecule. Specific examples of the crosslinking agents include aliphatic dialdehydes such as glutaraldehyde, glyoxal and malonic aldehyde; imidoesters; bifunctional acylating agents such as nitrophenyl esters of dicarboxylic acids, phenyl-2,4-disulfonyl chloride and α-naphthyl-2,4-disulfonyl chloride; bifunctional isocyanates such as xylene diisocyanates, toluene-2,4-diisocyanate, 3-methoxydiphenylmethane-4,4'-diisocyanate, 2,2'-dicarboxy-4,4'-azophenyl diisocyanate and hexamethylene diisocyanate; bifunctional aryl halides such as p,p'-difluoro-m,m'-dinitrodiphenyl sulfone and 1,5-difluoro-2,4-dinitrobenzene; bifunctional alkyl halides such as 2,2'-dicarboxy-4,4'-diiodoacetamidoazobenzene, N,N'-dibromoacetylphenylhydrazine, 1,2-di(bromoacetyl)amino-3-phenylpropane and N,N'-di(iodoacetyl)-polymethylenediamine; and bifunctional maleimide derivatives such as N,N'-(1,3-phenylene) bismaleimide, N,N'-(1,2-phenylene)bismaleimide, azophenyldimaleimide, N,N'-hexamethylenebismaleimide and bis(N-maleimidomethyl)ether. Expecially preferred crosslinking agents are aliphatic dialdehydes such as glutaraldehyde, glyoxal and malonic aldehyde.

By the use of the copolymer adsorbent of this invention, it is possible to effectively purify blood. In practicing purification of blood, for example, there is provided a blood circulation circuit comprising a blood vessel in a living body and a column packed with the adsorbent of this invention and connected through the circulation passages with the blood vessel. To the blood, an anticoagulant such as heparin is added in an amount of 1 to 5 Units per 1 ml of blood so that the blood can be kept uncoagulated, and the blood is circulated by a blood pump.

With respect to methods for removing toxic organic compounds from blood by adsorption, U.S. Pat. No. 3,794,584 discloses a method for removing phenobarbital and glutethimide present excessively in blood in which method a porous copolymer of styrene-ethylvinylbenzene-divinylbenzene having an average pore diameter of 100 Å or less is used as the adsorbent. By the use of the copolymer as disclosed in said U.S. patent, however, as will be seen from Comparative Examples given later, it is very difficult to remove toxic compounds adsorbed on the proteins present in blood.

On the other hand, it is disclosed in "Laboratory Diagnosis of Disease by Toxic Agents" written by W.

Sunderman & F. W. Sunderman Jr. and published by Warren H. Green Inc., St. Louis, Missouri, U.S.A. that toxic organic compounds such as phenobarbital and glutethimide can be removed from blood by haemodialysis to such an extent that the concentration in the blood of such organic compounds is near 3 mg/dl through this concentration may vary depending on their bonding constants to plasma proteins. From this fact, it is understood that in the blood a part of the toxic compounds exists in such a state that they are adsorbed on the proteins, though the amount of toxic compounds adsorbed may vary depending upon their inherent bonding constant to the proteins, while the remaining part thereof exists in a free state, and that the part in a free state can be removed by dialysis.

Accordingly, it is important in the art to remove the toxic compounds present in the state that they are adsorbed on the proteins. However, as described, the toxic compounds adsorbed on the proteins present in blood cannot be removed by the haemodialysis and the method of U.S. Pat. No. 3,794,584 as well as any other conventional methods.

According to the present invention, by the use of a specific porous copolymer as defined herein, the organic compounds (e.g. toxic compounds) adsorbed on the proteins (e.g. alubumin) in intercellular and/or extracellular liquids (e.g. blood) can surprisingly be effectively removed. Furthermore, it is noted that when the adsorption using the present porous copolymer is applied to the patients suffering from uremia, coma of liver cirrhosis and coma of fulminant hepatitis, unknown toxic substances, some of which are believed to be induced by the above-mentioned diseases and present in the blood in a state that they are adsorbed on the plasma proteins, may be effectively removed.

Desorption of organic compounds which have been adsorbed on the adsorbent of this invention may be effected by elution using methanol, ethanol, acetone, acetonitrile, propylalcohols or the like.

Other objects, features and advantages of this invention will be better understood from the description taken in connection with the accompanying drawings in which.

Figure 1:
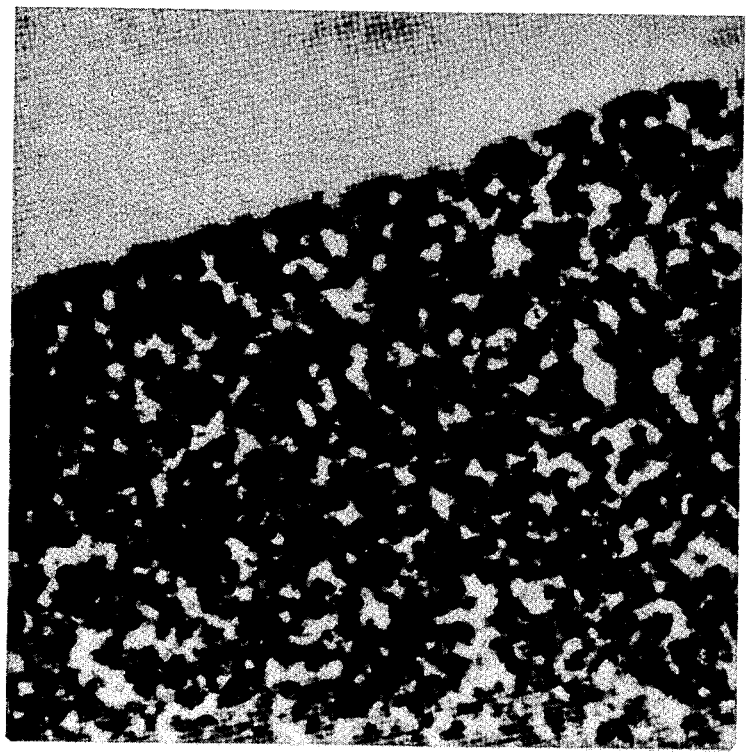
FIG. 1 is a microphotograph of the internal structure of the porous copolymer of this invention, the microphotograph being taken by a transmission-type electron microscope at a magnification of 33,000.

Reference numeral 1 designates an adsorbent according to the present invention, on which adsorbent a plasma protein may be adsorbed and fixed by a cross-linking agent such as glutaraldehyde. Reference numeral 2 designates an outer cylinder, 3 designates nozzle clamping rings, 4 designates an inlet or outlet for an intracellular or extracellular liquid or blood, 5 designates meshes for holding the adsorbent, 6 designates rings with which the meshes are welded, and 7 and 8 designate silicone packings for tightening the rings.

The purifier apparatus is packed with the dry copolymer at a bulk density of 20 to 500 g, preferably 50 to 400 g and more preferably 70 to 300 g per liter of the volume of the column.

By the use of this purifier apparatus, 300 mg of total bilirubin per 100 g of adsorbent can be removed by adsorption. In an experiment made on purification of ascites of a patient suffering from uremia, coma of liver cirrhosis and coma of fulminant hepatitis, it has been observed that in addition to bilirubin, uric acid is effectively removed by adsorption. It is noted that a number of other toxic metabolites bonded to serum albumin in the manner similar to that in the case of bilirubin can be removed using the above-mentioned purifier apparatus. After the purification of the liquid has been carried out using this purifier apparatus, there are not observed significant changes with respect to the properties of electrolytes in the plasma liquid and biochemical data etc. of the plasma liquid.

When the adsorbent of this invention is used in combination with microencapsulated activated carbon, alumina, silica and/or the like, there can be obtained synergistic effects for removing unknown toxic substances from the patients suffering from renal and/or hepatic trouble to effectively remedy the patients. In this case, the copolymer of the invention may be packed, in the purifier apparatus, together with a conventional adsorbent. When the copolymer of this invention is used in combination with other adsorbent, it is necessary for attaining the intended purpose of this invention to use the copolymer of this invention in an amount of at least 30% by volume per total volume of the adsorbents.

This invention will be further illustrated by the following Examples, which by no means limit the scope of the invention.

EXAMPLE 1

100 g of divinylbenzene (having a purity of 56% and containing 44% vinylethylbenzene; hereinafter referred to as "56% divinylbenzene"), 300 g of dioctyl phthalate and 1 g of azobisisobutyronitrile were charged in a 3 liter three-necked flask equipped with a reflux condenser, a stainless steel stirrer having two blades and a thermometer. In addition thereto, 1.5 g of partially saponified polyvinyl alcohol (having a viscosity of 23 cps and a degree of saponification of 88%) and 60 g of sodium chloride in 1,500 g of distilled water were added and the mixture was heated at 60° C. for one hour, at 70° C. for two hours, at 80° C. for two hours, and at 90° C. for four hours, while stirring at 250 rpm. During the course of the above reaction, the reaction mixture was sampled at predetermined intervals, followed by extraction of the sampled reaction mixture with benzene. The extract was analyzed by gas chromatography to determine the quantities of the monomers remaining unreacted. From the analysis data, the polymerization rate of the monomers employed was obtained. As a result, it was confirmed that under the above-mentioned reaction conditions, the yield of the copolymer was higher than 98%. The product copolymer was obtained in the form of substantially spherical granules having a diameter in the range of from 60μ to 500μ. The product in the wet state was subjected to classification by sieves, and then the unreacted monomers, liquid and the like were removed by acetone. Part of the product was dried at 60° C. for 18 hours under reduced pressure and used as a sample to be measured with respect to pore characteristics as mentioned below. The remaining copolymer was repeatedly washed with distilled water.

As a result of the measurement of pore characteristics using a porosimeter as described before, it was found that the resulting copolymer had a bulk density of 0.16, an average pore diameter of 2,500 Å and a total pore volume of 2.55 ml/g. It was also found that the volume of pores having a pore diameter in the range of 1,250 Å to 5,000 Å was 0.84 ml/g. This porous copolymer will be hereinafter referred to as "R-1".

3 mg of phenobarbital and 0.3 mg of Indocyanine Green dye which are both liable to be adsorbed onto proteins were dissolved into 150 ml of bovine blood containing heparin as an anticoagulant to obtain a mother liquid for the adsorption test. Into this mother liquid 2 g of the porous copolymer R-1 (having a grain diameter in the range of 210μ to 420μ) were added, and the obtained mixture was shaken at room temperature for 2 hours to effect adsorption. The supernatant was separated and the Indocyannine Green and phenobarbital remaining in the plasma were measured by spectrophotometry and gas chromatography, respectively. The rate of the adsorption were calculated in accordance with the following equation:

Rate of adsorption $(\%) = (A - B/A) \times 100$ wherein
A: concentration of the organic compound to be adsorbed in the blood before treated
B: concentration of the organic compound in the blood after treated.

Results are shown in Table 1.

In the biochemical data of the blood between before and after the adsorption operation, there were observed substantially no changes except for slight reduction in the total amounts of proteins and the number of blood cells.

EXAMPLE 2

10 g of hydroxyapatite, 10 g of hydroxymethyl cellulose, 20 g of sodium chloride and 2,000 ml of distilled water were charged in a flask similar to that used in Example 1 and after a homogenous solution was obtained by stirring thereof, into this solution was added at a stroke a solution comprising 36 g of 56% divinylbenzene, 64 g of styrene, 88 g of toluene, 132 g of isooctanol and 1 g of benzoyl peroxide while stirring at 200 rpm. The reaction was carried out at 60° C. for one hour, at 70° C. for two hours, at 80° C. for two hours and at 90° C. for two hours. After subjected to extraction with acetone the reaction product was washed with distilled water to obtain a porous copolymer. The porous copolymer thus obtained had a grain diameter in the range of 90μ to 500μ, an average pore diameter of 600 Å, a total pore volume of 1.46 ml/g and a bulk density of 0.18. It was also found that the volume of pores having a pore diameter in the range of 300 Å to 1,200 Å was 0.66 ml/g. This porous copolymer will be hereinafter referred to as "R-2".

Using the porous copolymer R-2 (having a grain diameter in the range of 210μ to 420μ) as an adsorbent, the same procedures as described in Example 1 were carried out. Results are shown in Table 1.

COMPARATIVE EXAMPLE 1

Using porous copolymer XAD-2 (having a grain diameter in the range of 210μ to 420μ) produced by Rohm and Haas Inc., U.S.A. the same procedures as described in Example 1 were carried out. Results are shown in Table 1.

Pore characteristics of this porous copolymer were measured in accordance with the same method as mentioned above, and it was found that this porous copolymer had an average pore diameter of 250 Å, a total pore volume of 0.60 ml/g, and a bulk density of 0.35. It was also found that the volume of pores having a pore diameter in the range of 125 Å to 500 Å was 0.33 ml/g.

COMPARATIVE EXAMPLE 2

Using porous copolymer XAD-4 (having a grain diameter in the range of 210μ to 420μ) produced by Rohm and Haas Inc., U.S.A. the same procedures as described in Example 1 were carried out. Results are shown in Table 1.

Pore characteristics of this porous copolymer were measured in accordance with the same method as mentioned above, and it was found that this porous copolymer had an average pore diameter of 250 Å, a total pore volume of 0.70 ml/g, and a bulk density of 0.31. It was also found that the volume of pores having a pore diameter in the range of 125 Å to 500 Å was 0.40 ml/g.

EXAMPLE 3

The same bovine blood as employed in Example 1 was centrifuged to separate and remove blood cells. The plasma liquid was used as a base of a mother liquid for the adsorption test. Into 150 ml of the plasma liquid were dissolved 0.3 mg of Indocyanine Green and 3 mg of phenobarbital to obtain a mother liquid for the adsorption test.

The thus prepared mother liquid was charged into an Erlenmeyer flask. While stirring by a magnetic stirrer at room temperature, the mother liquid was circulated at a flow rate of 5 ml/min through a purifier apparatus shown in FIGS. 2 and 3 and packed with 2 g of the porous copolymer R-1 (having a grain diameter in the range of 210μ to 420μ) prepared in Example 1.

After two-hour circulation, the concentrations of the organic compounds in the mother liquid were measured by spectrophotometry and gas chromatography. The rate of the adsorption was calculated in the similar manner as in Example 1, and at the same time the biochemical data were measured before and after the adsorption operation. Results are given in Table 2.

The excellent effectiveness of the porous copolymer to remove the organic compounds adsorbed on the proteins was clearly observed. Before and after the adsorption operation, there were substantially no changes on the biochemical data.

EXAMPLE 4

The same procedures as employed in Example 3 were carried out except that 2 g of the porous copolymer R-2 (having a grain diameter in the range of 210μ to 420μ) prepared in accordance with Example 2 was used as the adsorbent. Results are shown in Table 2.

COMPARATIVE EXAMPLE 3

The same procedures as employed in Example 3 were carried out except that 2 g of the porous copolymer XAD-2 (having a grain diameter in the range of 210μ to 420μ) employed in Comparative Example 1 was used as the adsorbent. Results are shown in Table 2.

COMPARATIVE EXAMPLE 4

The same procedures as employed in Example 3 were carried out except that 2 g of the porous copolymer XAD-4 (having a grain diameters in the range of 210μ to 420μ) employed in Comparative Example 2 was used as the adsorbent. Results are shown in Table 2.

EXAMPLE 5

300 ml of plasma obtained from a human body to which plasma had been added sodium citrate were added to 100 ml of the copolymer R-1 prepared in accordance with Example 1. The mixture was allowed to stand at 37° C. for 1 hour and then washed with 3 liters of a 0.1 M phosphate buffer solution having a pH value of 7.2.

Figure 2:
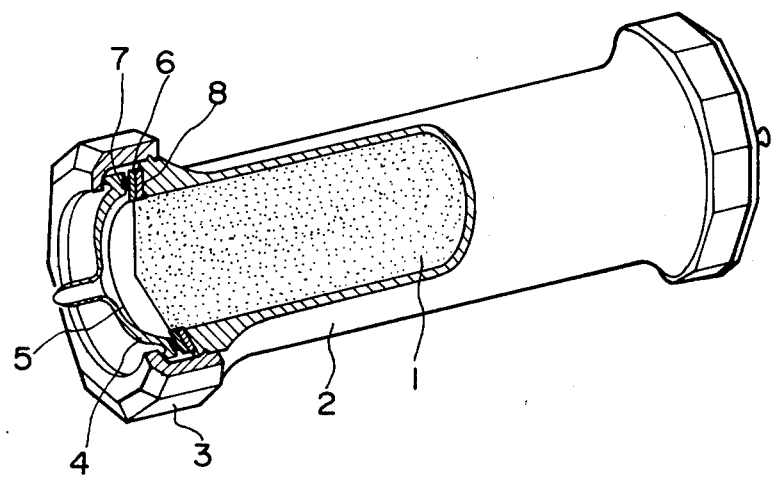
FIG. 2 is a diagrammatic perspective view of one form of the purifier apparatus packed with the adsorbent of this invention, with its part cut-away to show the internal structure.
Figure 3:
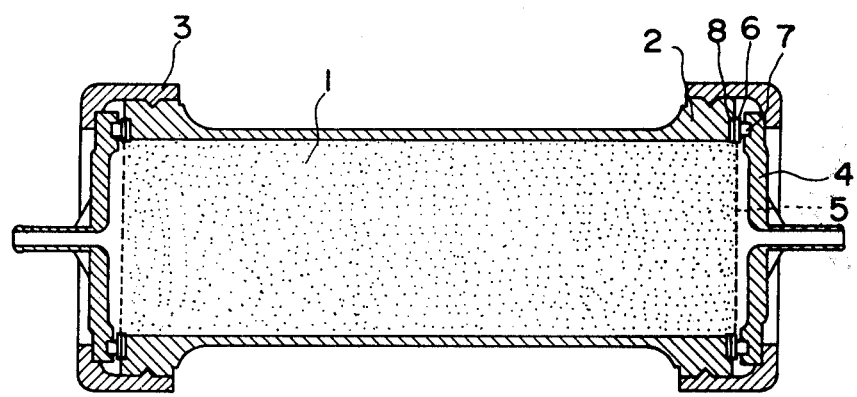
FIG. 3 is a longitudinal cross-section of the purifier apparatus as shown in FIG. 2.

Thereafter, the adsorbent was sieved to obtain its portion having a grain diameter in the range of 210μ–420μ. The portion was immersed in 1 liter of a 0.1 M phosphate buffer solution having a pH value of 7.2 and containing 2.5% of glutaraldehyde and allowed to stand at 37° C. for 1 hour. The thus obtained adsorbent was throughly washed with 10 liters of a physiological sodium chloride solution and then packed in a housing of the column as shown in FIGS. 2 and 3.

To fresh bovine blood was added 5 Units of heparin/ml of blood. In the resultant was dissolved unconjugated bilirubin sold by Sigma Inc. in U.S.A. in an amount of 10 mg per 100 ml of the blood. The resulting blood solution was passed through the housing packed with the pre-treated adsorbent R-1 at a flow rate of 100 ml/min.

After 10 minutes, the difference in bilirubin concentration between the blood solutions respectively at the inlet and outlet of the housing was measured. The concentration of bilirubin measured at the outlet was 67% of that measured at the inlet.

EXAMPLE 6

The same flask as used in Example 1 was charged with 10 g of hydroxylapatite, 10 g of hydroxyethyl cellulose having a viscosity of 250 cps as measured at 20° C. with respect to a 2% aqueous solution thereof. 20 g of calcium chloride and 2,000 liters of distilled water, and the mixture was stirred at 70° C. to form a homogeneous solution. Then, the liquid temperature was lowered to 30° C., and while the aqueous solution was being agitated at 300 rpm, a homogeneous solution composed of 40 g of acrylonitrile, 10 g of ethylene glycol dimethylacrylate, 50 g of styrene, 350 g of chlorobenzene, 0.25 g of tert-butyl pervalerate and 0.75 g of benzoyl peroxide was added at a stroke to the above aqueous solution. The reaction was carried out according to the predetermined temperature schedule; namely, at 30° C. for 30 minutes, at 40° C. for 1 hour, at 50° C. for 2 hours, at 60° C. for 2 hours, at 70° C. for 2 hours and at 80° C. for 2 hours. The resulting copolymer was sufficiently washed with water and subjected to measurements of pore characteristics. It was found that the grain diameters were distributed in the range of 90 to 260μ and the copolymer was characterized by an average pore diameter of 900 Å and a total pore volume of 2.12 ml/g. It also was found that the volume of pores having a pore diameter in the range of 450 to 1,800 Å was 1.06 ml/g. This porous copolymer will be referred to as "R-3" hereinafter.

The same procedures as employed in Example 3 were carried out except that the porous copolymer R-3 (having a grain diameter in the range of 210μ to 420μ) was used. Results are shown in Table 2.

EXAMPLE 7

A mixture of 40 g of styrene, 40 g of n-butylstyrene, 20 g of trimethylolpropane trimethacrylate, 150 g of toluene, 150 g of heptane and 1 g of benzoyl peroxide was polymerized in an aqueous solution composed of 2 liters of pure water, 20 g of carboxymethyl cellulose having a viscosity of 300 cps as measured at 20° C. with respect to a 2% aqueous solution thereof and 40 g of sodium chloride. The temperature schedule of polymerization and the post treatment were the same as described in Example 1. The pore characteristics of the resulting copolymer were as follows.

Average pore diameter: 5,000 Å
Total pore volume: 2.42 ml/g
Volume of pores having a pore diameter in the range of 2,500 to 10,000 Å: 1.36 ml/g The porous copolymer will be hereinafter referred to as "R-4". This porous copolymer "R-4" was sieved to obtain its portion having a grain diameter in the range of 210 to 420μ. The same procedures as employed in Example 3 were carried out thereafter except that the above obtained portion was used as the adsorbent. Results are shown in Table 2.

EXAMPLE 8

10 g of styrene, 8 g of N-vinylpyrrolidone, 2 g of polyethylene glycol dimethacrylate (molecular weight of 600) and 0.2 g of 2-cyano-2-propylazoformamide were dissolved in 60 g of a mixed organic liquid of 30 g of ethyl acetate and 30 g of diethyl phthalate and the resulting solution was charged into a 100 ml pressure-resistant glass ampoule. The ampoule was then sealed and heated at 120° C. for 1.5 hours. The reaction mixture was treated in the same manner as in Example 1 to yield a porous copolymer. The physical properties of the copolymer were as follows:

Average pore diameter: 930 Å
Pore volume: 0.86 (cm$^3$/g)
Bulk density: 0.17

This porous copolymer will be hereinafter referred to as "R-5". This copolymer was sieved to obtain its portion having a grain diameter in the range of 210 to 420μ. The same procedures as employed in Example 3 were carried out thereafter except that the above-obtained portion was used as the absorbent. Results are shown in Table 2.

EXAMPLE 9

A monomer mixture indicated in Table 3 was copolymerized by the same procedures as described in Example 1. This copolymer was sieved to obtain its portion having a grain diameter in the range of 50 to 100μ. This portion was packed in a glass column with a diameter of 2 cm and a length of 50 cm and was equilibrated with a 0.1 M/l Tris buffer solution having a pH value of 8.0.

To the column at its top end was added 10 ml of an aqueous solution containing 10 mg of albumin of bovine serum and 14 mg of sodium lauryl sulfate labeled with isotope. Then, 200 ml of the same Tris buffer solution as used for the equilibration of the column was passed through the column at a flow rate of 1 ml/min. The measurement of the eluate from the outlet of the column was done. As a result, 8.2 mg of albumin of bovine serum and 2.1 mg of sodium lauryl sulfate were found by the measurements using Lowry method and a liquid scintillation counter, respectively.

EXAMPLE 10

A monomer mixture indicated in Table 3 was copolymerized by the same procedures as described in Example 1. This copolymer was sieved to obtain its portion having a grain diameter in the range of 50 to 100μ.

Thereafter the same procedures as described in Example 9 was repeated except that the above-mentioned portion of the copolymer of the monomer mixture indicated in Table 3 was employed. The same measurement of the eluate from the outlet of the column as in Example 9 was done. 7.4 mg of alubmin of bovine serum and 1.3 mg of sodium lauryl sulfate were found in the eluate.

What is claimed is:

1. An adsorbent for adsorbing thereonto organic compounds from plasma proteins in blood on which proteins the organic compounds are adsorbed, said adsorbent comprising a porous copolymer produced by copolymerizing a mixture of monomers consisting essentially of 2% to 99% by weight of at least one cross-linkable monomer and 1% to 98% by weight of at least one mono-ethylenically unsaturated monomer, said porous copolymer having pores of an average pore diameter (d) in the range of from 600 Å to 5,000 Å, the volume of pores of a pore diameter in the range of from 0.5 d to 2 d being not more than 60% of the total volume in said porous copolymer.

2. An adsorbent as claimed in claim 1, wherein the total pore volume per 1 g of the porous copolymer in the dry state is in the range of $0.15\sqrt{X}$ ml to $1.3\sqrt{X}$ ml in which X stands for a percentage by weight of the cross-linkable monomer based on the total weight of the monomers.

3. An adsorbent as claimed in any one of claims 1 and 2, wherein said mono-ethylenically unsaturated monomer is selected from styrene, styrenes substituted with 1 to 3 straight chain or branched ($C_1$-$C_5$) alkyl groups and mixtures thereof.

Table 1

|  | Mother Liquid | Example 1 | Example 2 | Comparative Example 1 | Comparative Example 2 |
|---|---|---|---|---|---|
| Adsorbent |  | R-1 | R-2 | XAD-2 | XAD-4 |
| Adsorption rate of Indocyanine Green, % |  | 81 | 72 | 4 | 2 |
| Adsorption rate of phenobarbital, % |  | 90 | 86 | 5 | 3 |
|  | Before Test | After Test | | | |
| Red blood corpuscle (number/μl) | 4,500,000 | 4,300,000 | 4,400,000 | 4,400,000 | 4,300,000 |
| Leucocyte (number/μl) | 7,500 | 7,100 | 6,800 | 7,100 | 7,000 |
| Blood platelet (number/μl) | 210,000 | 150,000 | 160,000 | 140,000 | 150,000 |
| Total protein (g/dl) | 7.2 | 6.9 | 6.8 | 6.9 | 7.0 |
| Sodium (m eq/l) | 139 | 139 | 138 | 138 | 139 |
| Potassium (m eq/l) | 4.7 | 4.6 | 4.6 | 4.5 | 4.6 |
| Calcium (m eq/l) | 4.3 | 4.0 | 3.9 | 4.0 | 4.0 |
| Urea nitrogen (mg/dl) | 15.0 | 14.8 | 14.6 | 14.4 | 14.8 |
| Creatinine (mg/dl) | 0.40 | 0.40 | 0.35 | 0.35 | 0.35 |

Table 2

|  | Mother Liquid | Example 3 | Example 4 | Comparative Example 3 | Comparative Example 4 | Example 6 | Example 7 | Example 8 |
|---|---|---|---|---|---|---|---|---|
| Adsorbent |  | R-1 | R-2 | XAD-2 | XAD-4 | R-3 | R-4 | R-5 |
| Adsorption rate of Indocyanine Green, % |  | 94 | 80 | 6 | 3 | 66 | 82 | 62 |
| Adsorption rate of phenobarbital, % |  | 95 | 86 | 8 | 5 | 78 | 88 | 76 |
|  | Before Test | After Test | | | | | | |
| Total protein (g/dl) | 7.2 | 6.9 | 6.8 | 6.8 | 7.0 | 6.9 | 6.9 | 6.8 |
| Sodium (m eq/l) | 139 | 138 | 137 | 138 | 139 | 138 | 138 | 137 |
| Potassium (m eq/l) | 4.7 | 4.5 | 4.6 | 4.5 | 4.6 | 4.6 | 4.6 | 4.5 |
| Calcium (m eq/l) | 4.3 | 4.0 | 3.9 | 4.0 | 4.0 | 4.0 | 3.9 | 4.1 |
| Urea nitrogen (mg/dl) | 15.0 | 14.7 | 14.6 | 14.6 | 14.8 | 14.8 | 14.7 | 14.6 |
| Creatinine (mg/dl) | 0.40 | 0.40 | 0.40 | 0.35 | 0.35 | 0.39 | 0.38 | 0.36 |

Table 3

| | Polymerization | | | Porous Polymer | | | |
|---|---|---|---|---|---|---|---|
| Example No. | Monomer Mixture (g) | Organic Medium (g) | Water (g) | Bulk Density | Particle Diameter (micron) | Average Pore Diameter (Å) | Pore Volume (cm³/g) |
| 9 | 2-Vinylpyridine (60) Divinylbenzene (22) Ethylstyrene (18) | sec-Butanol (150) Cyclohexanol (150) | 2200 | 0.18 | 40–280 | 2500 | 1.88 |
| 10 | Styrene (70) Ethylene glycol diacrylate (30) | Nitroethane (200) Heptane (100) | 2000 | 0.16 | 40–200 | 820 | 1.96 |

4. An adsorbent as claimed in any one of claims 1, 2 and 3, wherein said cross-linkable monomer is at least one member selected from the group consisting of divinylbenzene, ethylene glycol diacrylate, polyethylene glycol diacrylates, ethylene glycol dimethacrylate, polyethylene glycol dimethacrylates, propylene glycol diacrylate, polypropylene glycol diacrylates, propylene glycol dimethacrylate, and polypropylene glycol dimethacrylates, the weight average molecular weight of each of the polyethylene glycol diacrylates, polyethylene glycol dimethacrylates, polypropylene glycol diacrylates and polypropylene glycol dimethacrylates being up to 1,500.

5. An adsorbent as claimed in claim 1, wherein said porous copolymer is blood plasma proteins adsorbed thereon and crosslinked with a crosslinking agent.

6. An adsorbent as claimed in claim 5, wherein said cross-linking agent is a member selected from the group consisting of aliphatic dialdehydes, imidoesters, bifunctional acrylating agents, bifunctional isocyanates, bifunctional aryl halides, bifunctional alkyl halides and bifunctional maleimide derivatives.

7. A purifier apparatus for an intracellular and/or extracellular liquid which comprises a housing having an inlet and an outlet for the intracellular and/or extracellular liquid and the porous copolymer defined in any of claims 1, 3, 4, 5 and said porous copolymer being contained in said housing.

8. A purifier apparatus as claimed in claim 7, wherein said porous copolymer is contained at a bulk density of 20 to 500 g per liter of the volume of said housing.

* * * * *